United States Patent [19]

Fujiwara et al.

[11] Patent Number: 5,273,039
[45] Date of Patent: Dec. 28, 1993

[54] SURGICAL MICROSCOPE APPARATUS HAVING A FUNCTION TO DISPLAY COORDINATES OF OBSERVATION POINT

[75] Inventors: Hiroshi Fujiwara, Hachiohji; Shigeo Tokunaga, Hino, both of Japan

[73] Assignee: Olympus Optical Co., Ltd., Tokyo, Japan

[21] Appl. No.: 978,162

[22] Filed: Nov. 17, 1992

Related U.S. Application Data

[63] Continuation of Ser. No. 592,787, Oct. 4, 1990, abandoned.

[30] Foreign Application Priority Data

Oct. 16, 1989 [JP] Japan .................................. 1-268823
Jul. 4, 1990 [JP] Japan .................................. 2-177133

[51] Int. Cl.$^5$ .............................................. A61B 6/00
[52] U.S. Cl. .................................. 128/653.1; 606/130
[58] Field of Search ................. 128/653.1; 606/130; 250/201.3

[56] References Cited

U.S. PATENT DOCUMENTS 5,050,608 9/1991 Watanabe et al. ................. 128/653.1

OTHER PUBLICATIONS

Friets et al., "A Frameless Stereotaxic Operating Microscope for Neurosurgery", IEEE Transactions on Biomedical Engineering, vol. 36, No. 6, Jun. 1989, pp. 608–617.

Kosugi et al., "An Articulated Neurosurgical Navigation System Using MRI and CT Images", IEEE Transactions on Biomedical Engineering, vol. 35, No. 2, Feb. 1988, pp. 147–152.

International Publication No. WO88/08282, Sundkvist, Hans, Apparatus for Making an Operating Site Nov. 3, 1988, pp. 1–6 and 4 drawings.

Primary Examiner—Ruth S. Smith
Attorney, Agent, or Firm—Cushman, Darby & Cushman

[57] ABSTRACT

A surgical microscope apparatus is equipped with movable member of a multi-articulation mechanism capable of moving a microscope in three dimensions. A plurality of detecting devices detect the moving directions and displacement distances of the movable members and a focusing device. A processing device calculates coordinates of an observation point relative to a standard point (an affected part of a patient) on the basis of detection signals provided from these detecting devices. An indicating device displays the coordinates of the observation point within an observation visual field of the surgical microscope. Furthermore, the plurality of detecting devices may be equipped to drive each of the movable members and the focusing device. The surgical microscope apparatus can then be moved to desired positions by driving each of the movable members and the focusing device with the detecting/driving devices.

13 Claims, 8 Drawing Sheets

TO PROCESSING
SECTION 18

TO CONTROL
SECTION 20

FIG. 11

FIG. 12 ature and the features and the
SURGICAL MICROSCOPE APPARATUS HAVING A FUNCTION TO DISPLAY COORDINATES OF OBSERVATION POINT This is a continuation of application Ser. No. 07/592,787, filed on Oct. 4, 1990 now abandoned.

BACKGROUND OF THE INVENTION a) Field of the Invention

The present invention relates to a surgical microscope apparatus capable of recognizing coordinates of an observation point.

b) Description of the Prior Art

In a surgical operation using a microscope, the general procedure is to locate an affected part by CT or MRT (nuclear magnetic resonance tomography), cut open a body surface and further dig the flesh down to the affected part for carrying out medical treatment. When the affected part is small or a a small opening is formed, however, approximate comprehension of the location of the affected part at the stage of the digging may make it difficult to locate directly to the affected part, thereby prolonging the time required for surgical operation or necessitating the repeat of the surgical operation.

Such a situation poses a vital problem especially in a surgical operation of an internal organ or may constitute a cause for failure of the surgical operation. Accordingly, it is a life-or-death problem in the literal sense for surgical operations of internal organs how to attain to affected parts without fail.

SUMMARY OF THE INVENTION

In view of the circumstance described above, it is a primary object of the present invention to provide a surgical microscope apparatus which is adapted to permit accurately comprehending positional relationship between an affected part and a point currently observed.

According to the present invention, this object is attained by equipping a surgical microscope with a multi-articulation mechanism capable of moving a microscope body in three dimensions relative to a stationary portion, a focusing device attached to the microscope body, a plurality of detecting displacement directions and displacement distances of movable members in the articulations from standard positions thereof as well as displacement direction and displacement distance of the microscope body from a standard position thereof, and a processing means capable of computing coordinates of an observation point relative to a standard point on the basis of detection signals provided from the detecting means.

In a preferred formation of the present invention, the surgical microscope apparatus is further equipped with an indicating means capable of displaying, within a visual field of the surgical microscope, the coordinates of the observation point relative to the standard point computed by the computing means.

The present invention makes it possible, in a surgical operation using a microscope, to attain to an affected part of interest without fail, form a small opening for surgical operation and allow surgical tools to attain speedily to the affected part. Further, the present invention makes it possible, even when the affected part is small, to find the affected part without fail and perform adequate medical treatment.

This and other objects as well as the features and the advantages of the present invention will become apparent from the following detailed description of the preferred embodiments when taken in conjunction with the accompanying drawings.

DESCRIPTION OF THE PREFERRED EMBODIMENTS

Figure 1:
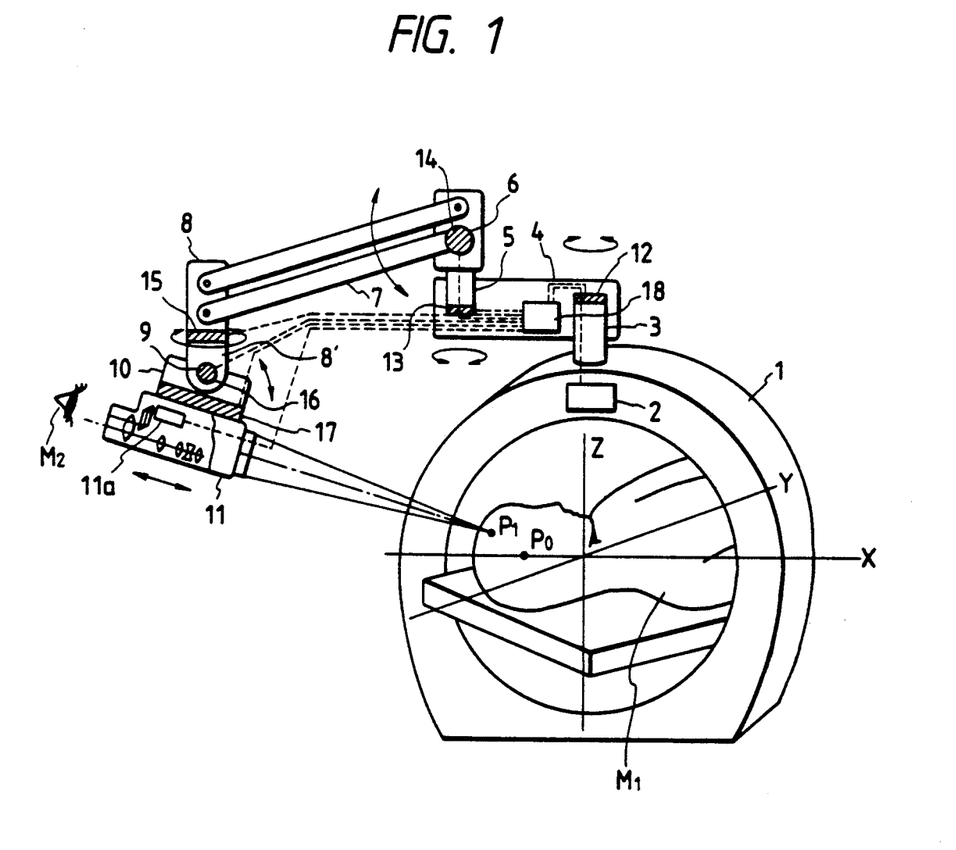
FIG. 1 is a schematic view illustrating an Embodiment 1 of the surgical microscope apparatus according to the present invention in the condition of use thereof.
Figure 2:
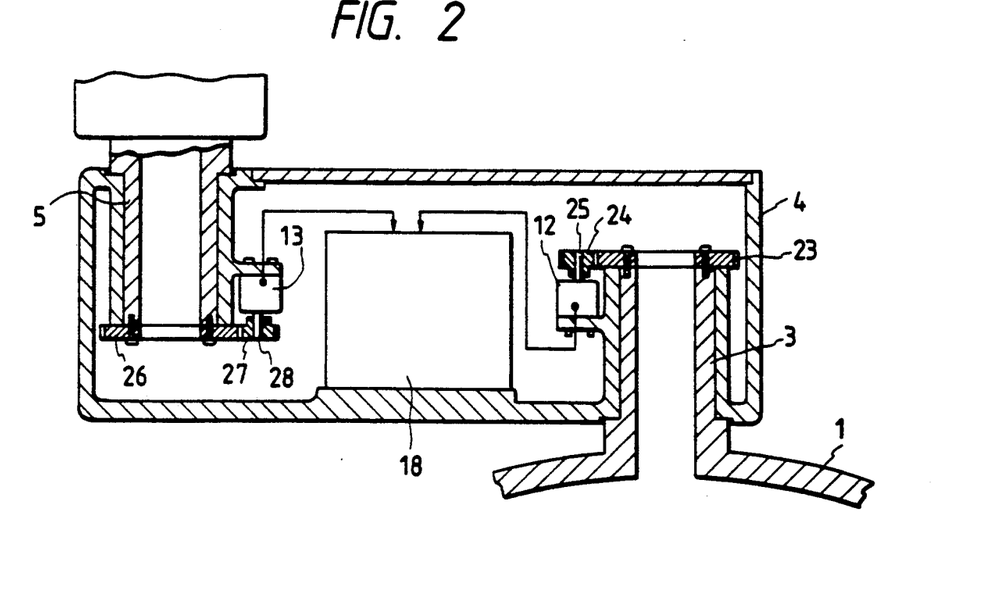
FIG. 2 is a sectional view illustrating the structure of a first arm together with a first shaft and a second shaft used in the Embodiment 1.
Figure 3:
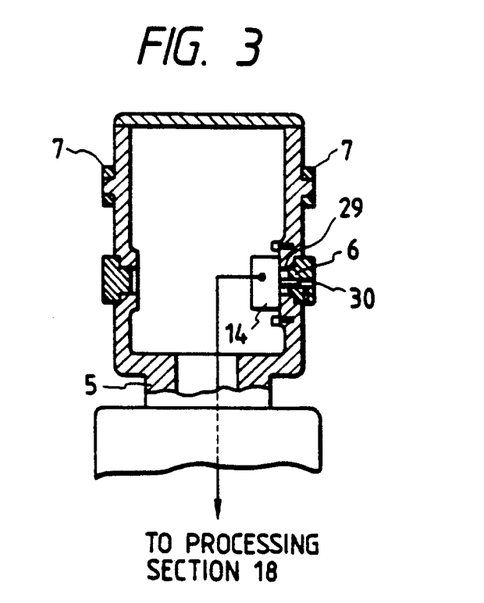
FIG. 3 is a sectional view illustrating the structure of the second shaft together with a third shaft used in the Embodiment 1.
Figure 4:
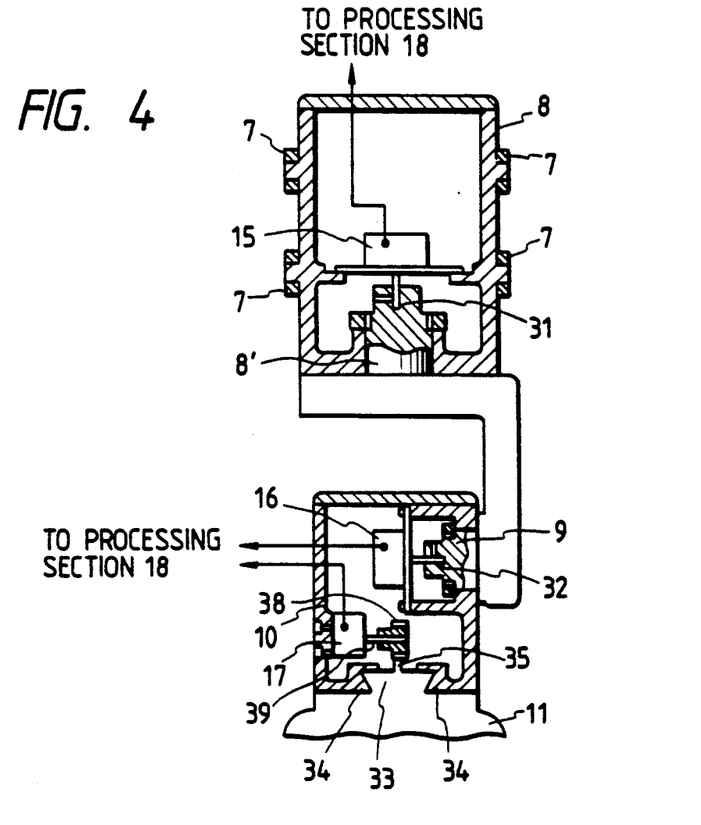
FIG. 4 is a sectional view illustrating the structure of a suspender together with a fourth shaft and a fifth shaft used in the Embodiment 1.
Figure 5:
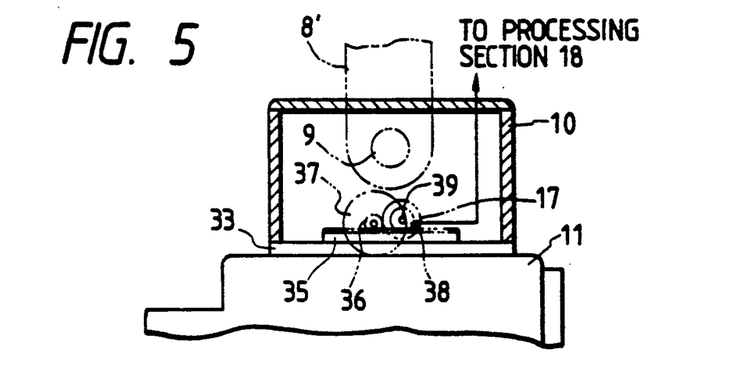
FIG. 5 is a sectional view illustrating the structure of a focusing section used in the Embodiment 1.

Now, the Embodiment 1 of the surgical microscope apparatus according to the present invention will be described below with reference to FIG. 1. In this drawing, the reference numeral 1 represents a computerized tomographer, the reference numeral 2 designates an image analyzing section, the reference numeral 3 denotes a first shaft arranged on a plane which is the same, as the photographing surface of the computerized tomographer 1, the reference numeral 4 represents a first arm connected to the first shaft 3, the reference numeral 5 designates a second shaft attached to an end of the first arm 4, the reference numeral 6 denotes a third shaft attached to an end of the second shaft 5, the reference numeral 7 represents a second arm rotatable around the third shaft 6, the reference numeral 8 designates a suspender connected to the second arm 7, the reference numeral 8' represents a fourth shaft connected to the suspender 8, the reference numeral 9 denotes a fifth shaft attached to an end of the fourth shaft 8' and the reference numeral 10 represents a focusing section which is connected to the fifth shaft 9 and provided for a microscope 11. The first shaft 3, the second shaft 5 and the fourth shaft 8' are rotatable around a vertical axis allowing for positioning the microscope 11 on a horizontal plane, whereas the third shaft 6 and the fifth shaft 9 are rotatable around a horizontal axis for allowing the determination of height and angle of elevation of the microscope 11. Accordingly, the microscope 11 can be located at optional positions in three dimensions, and the optical axis thereof can be set in an optional direction by using the multi-articulation mechanism composed of the articulations of the first shaft 3, the second shaft 5, the third shaft 6, the fourth shaft 8' and the fifth shaft 9 as well as the first arm 4, the second arm 7 and the suspender 8. The reference numerals 12, 13, 14, 15 and 16 represent detecting means composed of rotary encoders or the similar devices which are arranged on the first shaft 3, the second shaft 5, the third shaft 6, the fourth shaft 8' and the fifth shaft 9 respectively, and capable of detecting rotating angles, rotating directions, etc. of said shaft. The reference numeral 17 designates a detecting means capable of detecting displacement distance, etc. along the optical axis of the microscope 11 moved by the focusing section 10. The reference numeral 18 denotes a processing section which is connected to all of the detecting means mentioned above, stores position data on an affected part $p_0$ in a patient $M_1$ preliminarily inputted with signals from the image analyzing section 2, computes displacement distance and position of the microscope 11 on the basis of detection signals provided from the above-mentioned detecting means 12 through 17, calculate positional coordinates (x, y and z) of an observation point $P_1$ relative to the affected part $P_0$ (standard or reference point), and outputs the position data on the observation point $P_1$ to a display section 11a composed of LED's or LCD's arranged on the microscope 11. Further, the display section composed of the LED's or LCD's arranged on the microscope 11 is adapted to display the coordinates of the observation point $P_1$ within the visual field for a surgeon $M_2$. In FIG. 2, the reference numerals 23 and 26 represent gears fixed to the ends of the first shaft 3 and the second shaft 5 respectively, and the reference numerals 24 and 27 designate pinions which are fixed to the ends of rotating input shafts 25 and 28 of the detecting means 12 and 13, and engaged with the gears 23 and 26 respectively. Accordingly, horizontal rotating angles of the first arm 4 and the second arm 7, i.e., rotating angles of the first shaft 3 and the second shaft 5 are transmitted through the gears, and detected by the detecting means 12 and 13 so that outputs corresponding to the rotating angles are input to the processing section 18. As shown in FIG. 3, the third shaft 6 is rotatably fitted into a fitting hole 29 formed in one end of the second shaft 5 and fixed to a rotating input shaft 30 of the detecting means 14 which is in turn fixed to the end of the second shaft 5. Therefore, motion of the second arm 7 on the vertical plane is converted into rotation of the third shaft 6 and angle of this rotation is detected directly by the detecting means 14 so that an output corresponding to angle of the rotation is inputted into the processing section 18. As shown in FIG. 4 and FIG. 5, the fourth shaft 8' is fixed to a rotation input shaft 31 of the detecting means 15 arranged in the suspender 8 so that rotating angle of the fourth shaft 8' is detected directly by the detecting means 15. An output corresponding to the rotating angle is input into the processing section 18. Similarly, the fifth shaft 9 is fixed to the rotating input shaft 32 of the detecting means 16 arranged in the focusing section 10 so that rotating angle of the fifth shaft 9 is detected by the detecting means 16.

Figure 6:
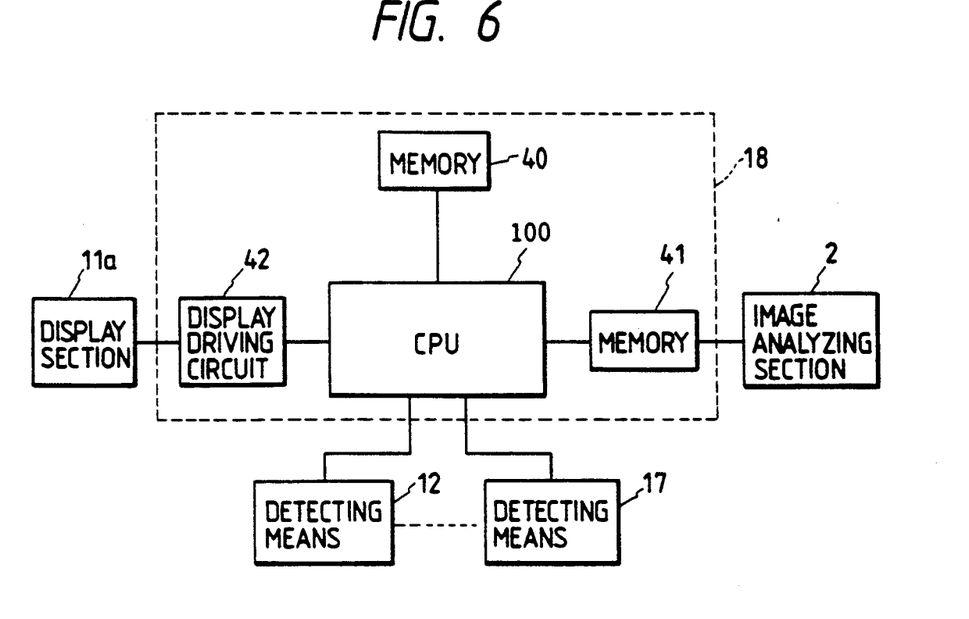
FIG. 6 is a block diagram illustrating an electric circuit used in the Embodiment 1.
Figure 7:
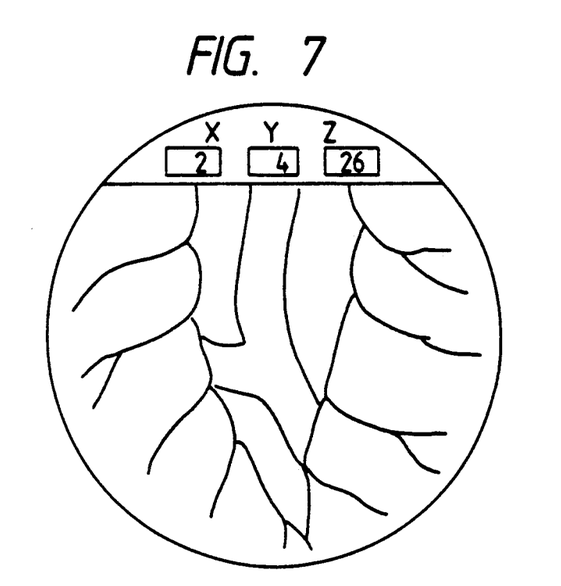
FIG. 7 is a diagram illustrating how coordinates of an observation point are displayed in an observation visual field in the Embodiment 1.

An output corresponding to said rotating angle is input into the processing section 18. Further, the reference numeral 33 represents a male dovetail integrated with the microscope 11 and the reference numeral 34 designates a female dovetail arranged in the focusing section 10, these dovetails being provided as guides for the microscope 11 for its motion along the optical axis. Further, the reference numeral 35 represents a rack arranged on the male dovetail 33, and the reference numeral 36 denotes a pinion which is meshed with the rack 35 and connected to a focusing handle 37 located outside the focusing section 10. Further, the reference numeral 38 designates a pinion meshed also with the rack 35 and fixed to a rotation input shaft 39 of the detecting means 17; which is composed of a rotary encoder or the similar device arranged in the focusing section 10, and capable of detecting rotating angle and rotating direction. When the focusing handle 37 is rotated, the microscope 11 is moved along the optical axis by the pinion 36 and the rack 35. This motion is converted into rotating motion by the rack 35 and the pinion 38. The latter motion is detected by the detecting means 17 as a new rotating angle, whereby an output corresponding to said new rotating angle is input into the processing section 18. In FIG. 6, the reference numeral 100 represents a CPU, the reference numeral 40 designates a memory storing data such as lengths of the arms, working distance of the objective lens, etc., the reference numeral 41 denotes a memory storing data on the location of the affected part $P_0$ provided from the image analyzing section 2, and the reference numeral 42 represents a display driving circuit for driving the display section 11a, these members composing the processing section 18. The rotating angle data provided from the detecting means 12 through 17 are taken into the CPU 100, which uses these data together with the data on the lengths of the arms, the working distance, etc. for conversion into data on displacement distance. The coordinates of the observation point $P_1$ are calculated on the basis of the data on the location of the affected point $P_0$ provided from the image analyzing section 2 and stored in the memory 41 plus said data on the displacement distance. Further, values of the coordinates are displayed on the display section 11a through the display driving circuit 42. FIG. 7 shows how the coordinates of the observation point $P_1$ are displayed within the visual field. In this drawing, the reference symbols X, Y and Z mean the axes of the coordinates shown in FIG. 1 and the numerical values represent distances along the axes as measured from the affected part $P_0$ to the observation point $P_1$. In the case exemplified in FIG. 7, the observation point $P_1$ is located above the affected part $P_0$.

Since the Embodiment 1 has the configuration described above, it determines location of the affected part $P_0$ as the standard point with the image analyzing section 2 and provides location data on said affected part $P_0$ to the processing section 18 after tomographing the patient $M_1$ with the computerized tomographer 1. On the other hand, location of the observation point $P_1$ as measured from the standard point is computed on the basis of the location data provided from the detecting means for the first shaft 3, the second shaft 5, the third shaft 6, the fourth shaft 8 and the fifth shaft 9 as well as that for the focusing section 10, and compared with the location data on the affected part $P_0$, whereby coordinates of the observation point $P_1$ are determined taking the affected point $P_0$ as standard. The coordinates data of the observation point $P_1$ are displayed in the visual field for the surgeon $M_2$ so that the surgeon $M_2$ can recognize the accurate coordinates of the observation point $P_1$ relative to the affected part $P_0$.

Since the surgical microscope apparatus according to the present invention allows the surgeon $M_2$ to accurately comprehend the positional relationship between the affected part $P_0$ and the observation point $P_1$ as described above, it helps the surgeon $M_2$ to bring a treating means or the similar device accurately and easily to the affected part $P_0$, thereby preventing risks such as failed operation and re-operation. Especially in cases of craniotomy, etc., the surgical microscope apparatus according to the present invention allows the surgeon $M_2$ to effectively cope with variation of location of affected parts caused by variation of internal pressures of cranium and bring the treating means or the similar device to the affected parts without fail even in such cases.

Figure 8:
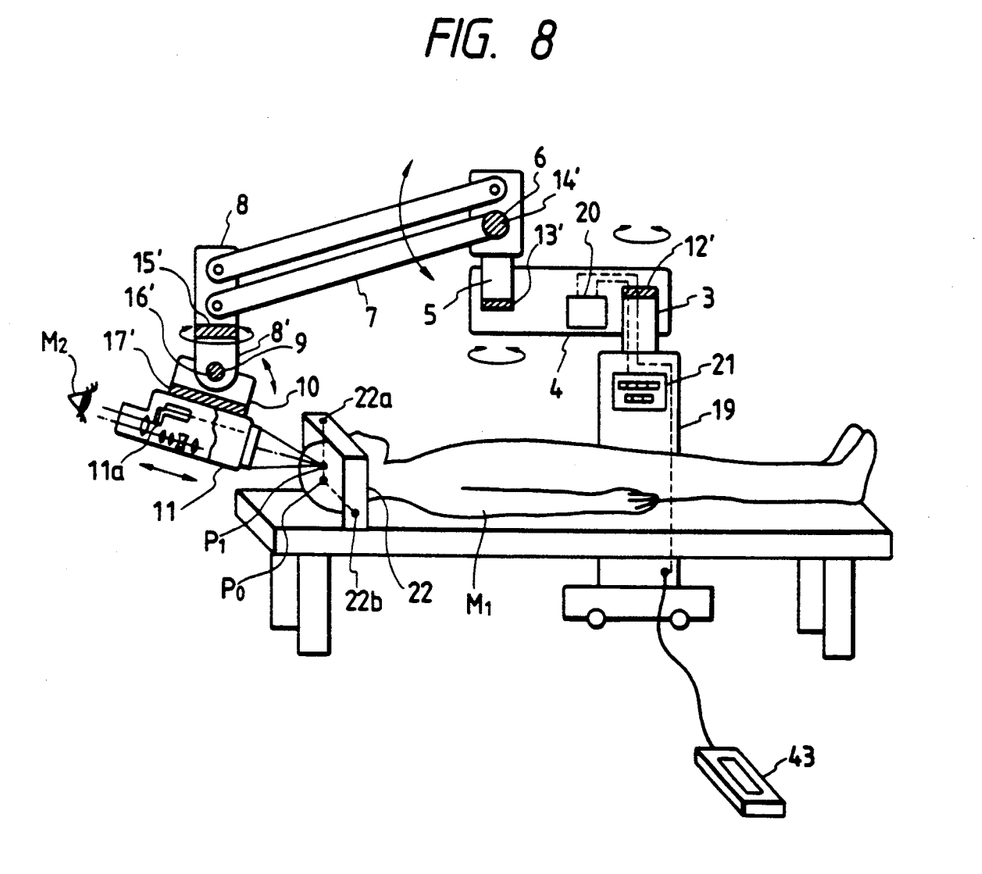
FIG. 8 is a schematic view illustrating an Embodiment 2 of the surgical microscope apparatus according to the present invention in the condition of use thereof.
Figure 9:
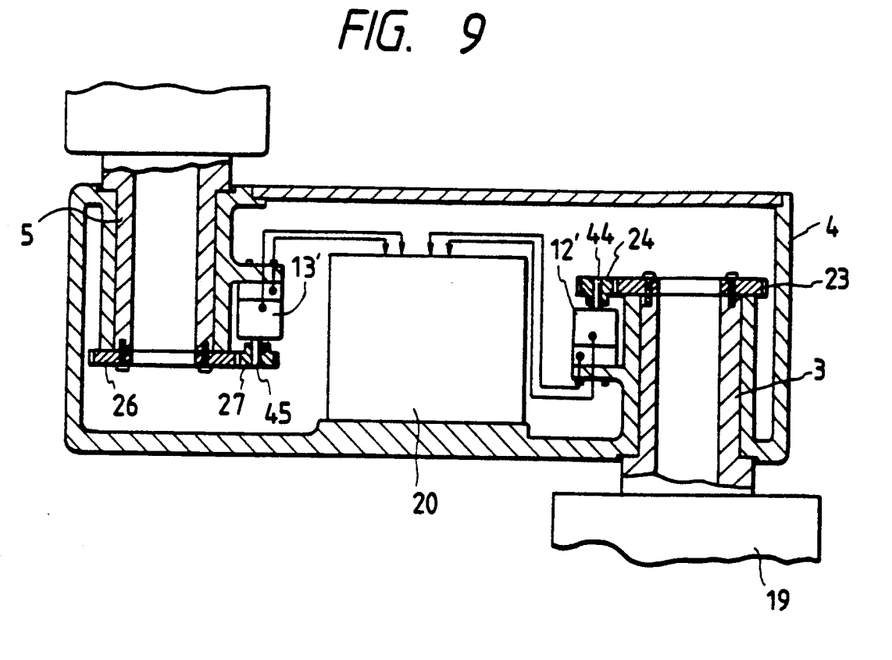
FIG. 9 is a sectional view illustrating the structure of the first arm together with the first shaft and the second shaft used in the Embodiment 2.
Figure 10:
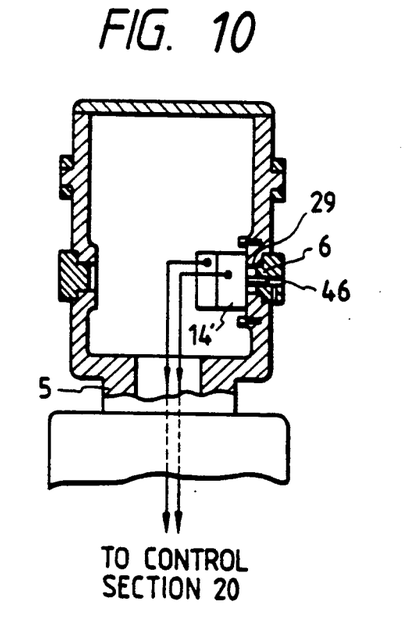
FIG. 10 is a sectional view illustrating the structure of the second shaft together with the third shaft used in the Embodiment 2.
Figure 11:
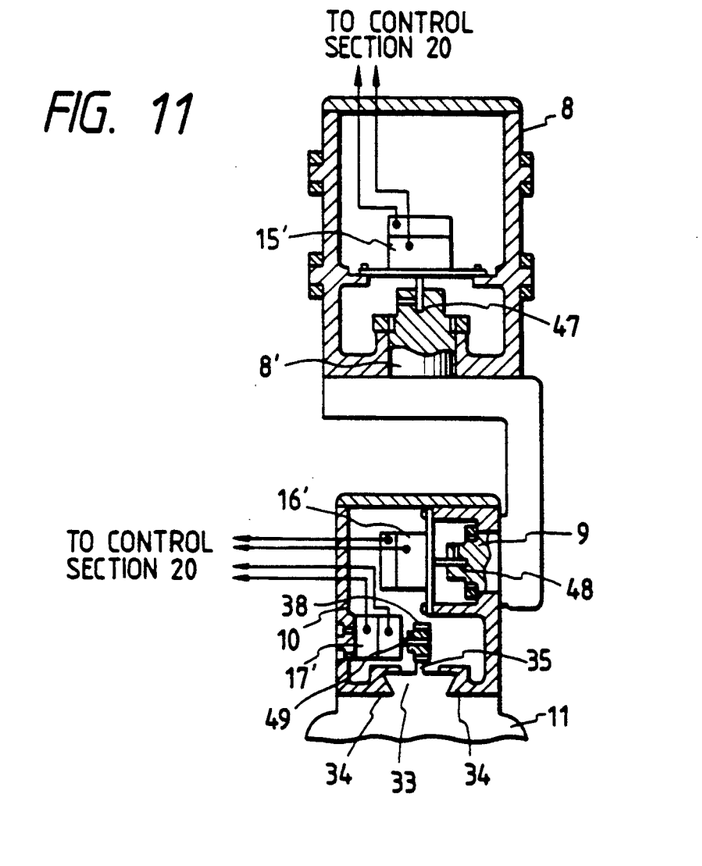
FIG. 11 is a sectional view illustrating the structure of the suspender together with the fourth shaft and the fifth shaft used in the Embodiment 2.
Figure 12:
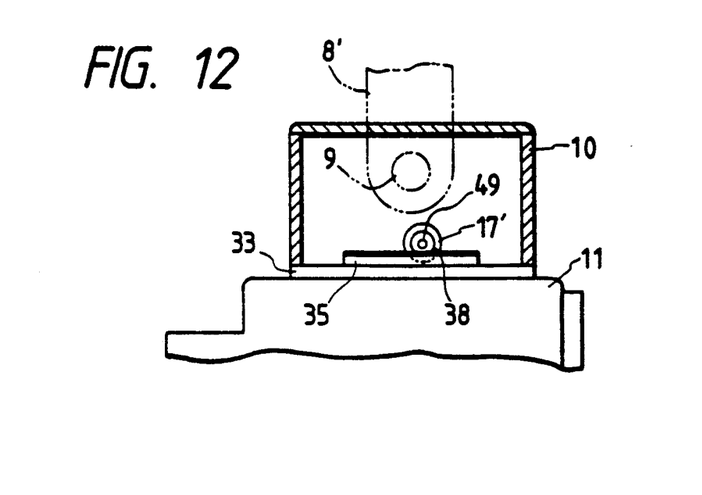
FIG. 12 is a sectional view illustrating the structure of the focusing section used in the Embodiment 2.
Figure 13:
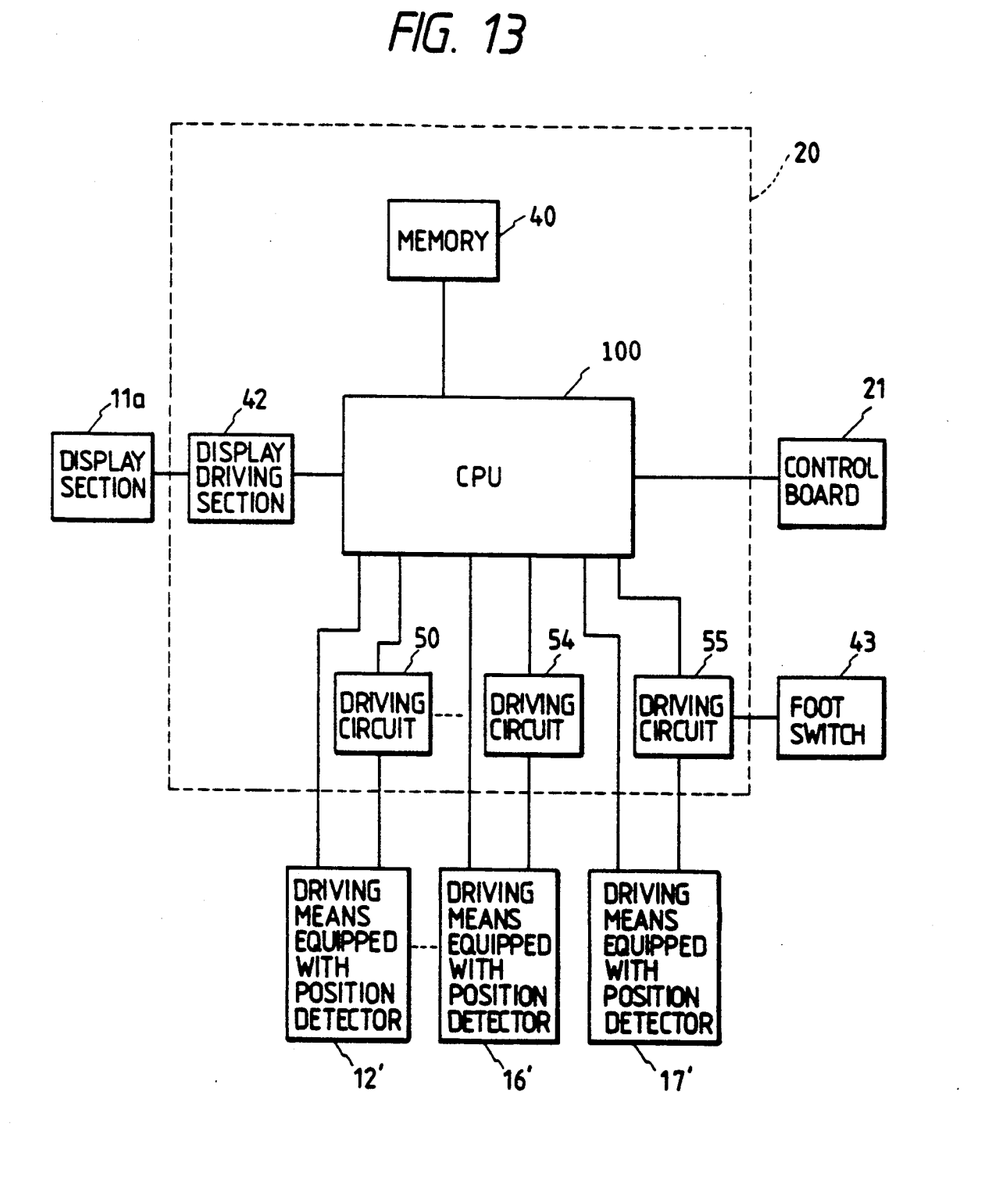
FIG. 13 is a block diagram illustrating the electric circuit used in the Embodiment 2.

FIG. 8 illustrates the Embodiment 2 of the surgical microscope apparatus according to the present invention. The multi-articulation mechanism which is so constructed as to be capable of sustaining the microscope 11 at optional height and in optional directions has the same fundamental structure as that in the Embodiment 1, and will not be described in particular. However, the first shaft 3 is mounted on a movable stand 19. Further, the reference numerals 12', 13', 14', 15', 16' and 17', representing driving means which are provided in place of the detecting means 12, 13, 14, 15, 16 and 17 respectively used in the Embodiment 1, have not only the same detecting functions as those of the detecting means but also functions to drive the individual movable members, and are connected to the control section 20. Accordingly, the coordinates of the point $P_1$ observed through the microscope 11 moved by using the multi-articulation mechanism are displayed on the display section 11a and the control section is further connected to a control board 21 which allows to input the coordinates of the observation point $P_1$. This control section 20 is adapted to be capable of calculating the positions of the shafts 3, 5, 6, 8 and 9 as well as that of the focusing section 10 corresponding to the inputted coordinates on the basis of the input signals from the control board 21, providing drive control signals to the detecting-driving means 12', 13', 14', 15', 16' and 17', and moving the microscope 11 to desired positions by using the multi-articulation mechanism. In addition, the focusing section 10 can be operated independently by using a foot switch 43 connected to the control section 20. The necessary part of the patient $M_1$ is covered with an indicating frame 22 which is equipped with a mark 22a for indicating the forward-backward and right-left directions of the affected part $P_0$ found by CT or MRT; as well as, a mark 22b for indicating the up-down direction of the affected part $P_0$ so that the surgeon $M_2$ can recognize the location of the affected part $P_0$. As shown in FIG. 9, the pinions 24 and 27 are fixed to rotating shafts 44 and 24 respectively of the driving means 12' and 13'. The driving means 12' and 13' are equipped with position detectors arranged on the first arm 4 so that the detecting-driving means 12' and 13' function, upon receiving signals from the control section 20, to rotate the shafts 3 and 5, and detect rotating angles of these shafts. An output corresponding to each of the rotating angles is input into the control section 20. As illustrated in FIG. 10 the third shaft 6 and the rotating shaft 46 of the detecting-driving means 14' are fixed to an end of the second shaft 5. In FIG. 11, the fourth shaft 8' and a rotating shaft 47 of the detecting-driving means 15' are arranged in the suspender 8, and a rotating shaft 48 of the detecting-driving means 16' is arranged in the focusing section 10. The detecting-driving means 14', 15' and 16' function, upon receiving signals from the control section 20, to rotate the shafts 6, 8' and 9, and detect the rotating angles of these shafts for providing outputs corresponding to the rotating angles to the control section 20. In FIG. 12, the pinion 38 is fixed to a rotating shaft 49 of the detecting-driving means 17' arranged in the focusing section 10. The detecting-driving means 17' functions, upon receiving a signal from the control section 20 and in cooperation with the pinion 38 and rack 35, to move the microscope 11 and detect position thereof for providing an output corresponding to the position of the microscope to the control section 20. In FIG. 13, the control section 20 is composed of the CPU 100, the memory 40, the display driving circuit 42, and driving circuits 50, 51, 52, 53, 54 and 55 which drive the detecting-driving means 12', 13', 14', 15', 16' and 17' respectively. Further, the foot switch 43 is adapted to operate the driving circuit 55 independently. When the CPU 100 receives a signal from the control board 21 or the surgeon $M_2$ operates the foot switch 43, the detecting-driving means 12' through 17' are operated by way of the driving circuits 50 though 55 so as to rotate the shafts. Thus, the observation point $P_1$ is displaced, and the focusing section 10 is moved for focusing the microscope 11. Further, similar to the case of the Embodiment 1, the rotating angle data provided from the detecting-driving means 12' through 17' are input into the CPU 100, and used for calculations together with the data on the lengths of the arms and the working distance. Calculated data on coordinates of the observation point $P_1$ are stored in the memory 40 and the display section 11a displays the coordinates of the observation point $P_1$ upon receiving a signal from the control board 21.

Now, functions of the Embodiment 2 will be described below. First, the location of the affected part $P_0$ is recognized as coordinates of a standard point in the forward-backward and right-left directions by operating the control board 21 with the observation point $P_1$ aligned with the indicating mark 22a. Then the location of the affected part $P_0$ is recognized as coordinates of the standard point in the up-down direction by operating the control board 21 with the observation point $P_1$ aligned with the indicating mark 22b. The affected part $P_0$ is determined and location data on the affected part $P_0$ is provided to the control section 20. The current location of the observation point $P_1$ is calculated by the control section 20 on the basis of the detecting signals from the detecting-driving means 12', 13', 14', 15', 16' and 17', and compared with the location data on the affected part $P_0$. The coordinates of the observation point $P_1$ are determined taking the affected part $P_0$ as standard and displayed in the visual field of the display section 11a of the microscope 11. Further, when it is desired to relocate the observation point $P_1$, the coordinates of a location are input from the control board 21. Then, the control section 20 calculates the positions of the shafts 3, 5, 6, 8 and 9 as well as that of the focusing section 10 corresponding to the new location, and provides the calculated results as driving control signals to the detecting-driving means 12', 13', 14', 15', 16' and 17'. Thus the observation point $P_1$ is relocated to the coordinates selected as a target. In addition, the focusing section 10 is adapted to be independently capable of bringing the target into focus as described above. In the Embodiment 2 also, the surgeon $M_2$ can bring the observation point $P_1$ to the affected part $P_0$ accurately and easily when the coordinates of the observation point $P_1$ are preliminarily matched with those of the affected part $P_0$, by operating the control board 21, and the microscope 11 is brought into focus on the body surface of the patient $M_1$, by operating the focusing section 10, the Embodiment 2 provides a great convenience by allowing the observation point $P_1$ to be easily shifted to the affected part $P_0$ simply by the focusing operation with the focusing section 10.

What is claimed is:

1. A multi-articulation support apparatus for determining an observation point of a surgical microscope, comprising:
   a surgical microscope;
   at least two moveable members, one of which is connected to said surgical microscope;
   a detecting means associated with each movable member for detecting the direction and distance of movement of each movable member; and
   a processing means for receiving coordinates of a slanted point and for calculating coordinates of an observation point of said surgical microscope based on said standard point and output signals from said detecting means.

2. An apparatus as in claim 1, further comprising:
   a focusing detecting means for detecting movement of said surgical microscope along its optical axis; and
   wherein said processing means calculates the coordinates of said observation point of said surgical microscope based on said standard point and output signals from said detecting means and said focusing detecting means.

3. An apparatus as in claim 2, further comprising:
   display means for displaying the coordinates of said observation point within an observational visual field of said surgical microscope.

4. An apparatus as in claim 2, wherein said movable member comprises:
   a first shaft rotatable around a vertical axis and connected to a first end of a first arm;
   a second shaft rotatable around a vertical axis and connected to a second end of said first arm;
   a third shaft rotatable around a horizontal axis and connected to said second shaft and a first end of a second arm;
   a fourth shaft rotatable around a vertical axis and connected to a second end of said second arm;
   a fifth shaft rotatable around a horizontal axis and connected to said fourth shaft and said surgical microscope.

5. An apparatus as in claim 4, wherein said first shaft is connected to a static base.

6. An apparatus as in claim 4, wherein said first shaft is connected to a moveable base.

7. An apparatus as in claim 2, further comprising driving means included in each detecting means and said focusing detecting means for moving said movable members.

8. An apparatus as in claim 7, further comprising:
   a control means for supplying coordinates of a target observation point as said standard point to said processing means and instructing said processing means to drive said driving means to locate said surgical microscope at said target observation point.

9. An apparatus as in claim 1, wherein the processing means stores the coordinates of an affected part of a patient as the standard point.

10. A multi-articulation support apparatus for determining an observation point of a surgical microscope, comprising:
    a surgical microscope;
    a first shaft rotatable around a vertical axis and connected to a first end of a first arm;
    a second shaft rotatable around a vertical axis and connected to a second end of said first arm;
    a third shaft rotatable around a horizontal axis and connected to said second shaft and a first end of a second arm;
    a fourth shaft rotatable around a vertical axis and connected to a second end of said second arm;
    a fifth shaft rotatable around a horizontal axis and connected to said fourth shaft and said surgical microscope;
    a detecting means associated with each of said first, second, third, fourth, and fifth shafts for detecting the direction and distance of movement of said first, second, third, fourth, and fifth shafts;
    a focusing detecting means for detecting movement of said surgical microscope along its optical axis;
    processing means for receiving coordinates of a standard point and for calculating coordinates of an observation point of said surgical microscope based on said standard point and output signals from said detecting means and said focusing detecting means; and
    display means for displaying the coordinates of said observation point within an observational visual field of said surgical microscope.

11. An apparatus as in claim 10, further comprising:
    a computerized tomographer; and
    wherein the first shaft is arranged in a plane of a photographic surface of said computerized tomographer.

12. A multi-articulation support apparatus a surgical microscope, comprising:
    a surgical microscope;
    a first shaft rotatable around a vertical axis and connected to a first end of a first arm;
    a second shaft rotatable around a vertical axis and connected to a second end of said first arm;
    a third shaft rotatable around a horizontal axis and connected to said second shaft and a first end of a second arm;
    a fourth shaft rotatable around a vertical axis and connected to a second end of said second arm;
    a fifth shaft rotatable around a horizontal axis and connected to said fourth shaft and said surgical microscope;
    a detecting means associated with each of said first, second, third, fourth, and fifth shafts for detecting the direction and distance of movement of said first, second, third, fourth, and fifth shafts;
    a focusing detecting means for detecting movement of said surgical microscope along its optical axis;
    driving means included in each detecting means and said focusing detecting means for rotating said first, second, third, fourth, and fifth shafts and for moving said surgical microscope along its optical axis;
    processing means for receiving coordinates of a standard point and for calculating coordinates of an observation point of said surgical microscope based on said standard point and output signals from said detecting means and said focusing detecting means;

a control means for supplying coordinates of a target observation point as said standard point to said processing means and instructing said processing means to drive said driving means to locate said surgical microscope at said target observation point; and display means for displaying the coordinates of said observation point within an observational visual field of said surgical microscope.

13. An apparatus as in claim 12, wherein the processing means stores the coordinates of an affected part of a patient as the standard point.

* * * * *

UNITED STATES PATENT AND TRADEMARK OFFICE
CERTIFICATE OF CORRECTION

PATENT NO. : 5,273,039
DATED : December 28, 1993
INVENTOR(S) : FUJIWARA ET AL

It is certified that error appears in the above-indentified patent and that said Letters Patent is hereby corrected as shown below:

Column 7 Claim 1 Line 25

Please Change "slanted" to —standard—.

Signed and Sealed this

Eleventh Day of October, 1994

Attest:

BRUCE LEHMAN

Attesting Officer    Commissioner of Patents and Trademarks